(12) United States Patent
Bernard et al.

(10) Patent No.: US 9,451,924 B2
(45) Date of Patent: Sep. 27, 2016

(54) SINGLE SCREEN MULTI-MODALITY IMAGING DISPLAYS

(75) Inventors: Sylvain Bernard, Buc (FR); Serge Louis Wilfrid Muller, Buc (FR); Vincent S. Polkus, Waukesha, WI (US); Xavier Bouchevreau, Buc (FR)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 735 days.

(21) Appl. No.: 12/650,070

(22) Filed: Dec. 30, 2009

(65) Prior Publication Data

US 2011/0157154 A1    Jun. 30, 2011

(51) Int. Cl.
| | |
|---|---|
| *G09G 5/14* | (2006.01) |
| *A61B 6/00* | (2006.01) |
| *G06T 7/00* | (2006.01) |
| *G06T 11/60* | (2006.01) |
| *A61B 8/00* | (2006.01) |
| *G06F 19/00* | (2011.01) |
| *A61B 6/02* | (2006.01) |
| *A61B 6/03* | (2006.01) |

(52) U.S. Cl.
CPC ............ *A61B 6/463* (2013.01); *A61B 6/5229* (2013.01); *A61B 8/00* (2013.01); *G06T 7/0024* (2013.01); *G06T 11/60* (2013.01); *A61B 6/025* (2013.01); *A61B 6/032* (2013.01); *A61B 6/037* (2013.01); *A61B 6/482* (2013.01); *A61B 6/502* (2013.01); *G06F 19/321* (2013.01); *G06T 2210/41* (2013.01)

(58) Field of Classification Search
CPC ....................................................... A61B 6/037

USPC ........................................ 345/634; 382/128
See application file for complete search history.

(56) References Cited

U.S. PATENT DOCUMENTS

| | | | | |
|---|---|---|---|---|
| 4,501,009 | A  * | 2/1985  | Abele ............................. | 378/19 |
| 5,592,237 | A  * | 1/1997  | Greenway et al. ........... | 348/716 |
| 5,749,364 | A  * | 5/1998  | Sliwa et al. .................. | 600/438 |
| 6,591,127 | B1 * | 7/2003  | McKinnon .................... | 600/411 |
| 7,020,313 | B2   | 3/2006  | Declerck et al. | |
| 7,822,241 | B2   | 10/2010 | Eck et al. | |
| 7,986,821 | B2 * | 7/2011  | DuGal .......................... | 382/128 |
| 8,160,314 | B2 * | 4/2012  | Ramamurthy et al. ....... | 382/128 |
| 2005/0111732 | A1* | 5/2005 | Mallya et al. ................ | 382/173 |
| 2006/0008174 | A1* | 1/2006 | Avinash et al. ............... | 382/275 |
| 2007/0027408 | A1* | 2/2007 | Fitzgerald et al. ........... | 600/587 |
| 2008/0267499 | A1* | 10/2008 | Deischinger et al. ........ | 382/173 |
| 2009/0012383 | A1* | 1/2009 | Virtue et al. .................. | 600/407 |
| 2009/0052753 | A1  | 2/2009 | Sugahara | |

(Continued)

OTHER PUBLICATIONS

EP Search Report, Application No. 10196213.2-1901 / 2341482, mailed Mar. 27, 2014; pp. 5.

*Primary Examiner* — Javid A Amini
(74) *Attorney, Agent, or Firm* — Fletcher Yoder, P.C.

(57) ABSTRACT

Methods and systems provide an integrated display, on a single screen, of images obtained from multiple modalities used in screening a subject. The methods and systems are usable with 2D, 3D, and 4D imaging, by which a single screen displays a screen image from a first modality. A window delineating an area of interest is placed on a first modality image from the first modality, and this area of interest is then displayed on a second modality image from a second modality, thereby providing a combined image representing the area of interest through both modalities. Preferably, the first modality image corresponds and/or is correlated with the second modality image.

14 Claims, 10 Drawing Sheets

(56) References Cited

U.S. PATENT DOCUMENTS

| | | | |
|---|---|---|---|
| 2009/0213140 A1* | 8/2009 | Ito et al. | 345/629 |
| 2009/0276045 A1* | 11/2009 | Lang | 623/14.12 |
| 2010/0053214 A1* | 3/2010 | Goto | 345/629 |
| 2010/0290693 A1* | 11/2010 | Cohen et al. | 382/134 |
| 2011/0040176 A1* | 2/2011 | Razansky et al. | 600/425 |
| 2011/0125526 A1* | 5/2011 | Gustafson | 705/3 |
| 2011/0263946 A1* | 10/2011 | el Kaliouby et al. | 600/300 |
| 2011/0305378 A1* | 12/2011 | Florent et al. | 382/130 |

* cited by examiner

64

66

68

70

SINGLE SCREEN MULTI-MODALITY IMAGING DISPLAYS

BACKGROUND

In general, the inventive arrangements relate to methods and systems for displaying images from multiple imaging sources on a single display, and more particularly, to methods and systems for displaying, on a single screen, a result of a first patient image scanning modality that can also display information from a different patient image scanning modality corresponding to a particular region of interest or volume of interest of a patient from a patient examination.

When examining and diagnosing medical patients, advanced imaging workflows can perform a first imaging modality examination on a patient followed by an additional imaging modality examination of that same patient. If both examinations depict a common anatomy of the patient, then the second examination can increase the sensitivity and/or specificity of the obtained images and/or facilitate better patient management decisions, particularly as provided by the multiple imaging information. One drawback, however, when obtaining multiple modality image sets is that it can increase the amount of data that needs to be analyzed and correlated, including by human operators.

One way to analyze multiple images acquired with multiple modalities consists of displaying images on side-by-side screens. However, this requires multiple screens, for which users must indirectly correlate findings from the separate modality images. In addition, relevant contextual information can be lost when a radiologist switches from reviewing one modality to reviewing another, particularly if there is primarily interest in only a single region or volume of interest.

Accordingly, it would be advantageous to provide improved methods and systems that can provide a single screen view of data and/or imagery received from a plurality of imaging modalities.

SUMMARY OF INVENTIVE ARRANGEMENTS

One embodiment of the inventive arrangements comprises a method of displaying image data of an imaged subject, comprising providing a first modality image, selecting an area of interest in the first modality image, providing a second modality image, and displaying the area of interest from the first modality image on the second modality image.

Another embodiment of the inventive arrangements comprises a system for displaying image data of an imaged subject, comprising a screen, a first imaging modality to provide a first modality image, a second imaging modality to provide a second modality image, and a selector to select an area of interest in the first modality image, wherein the screen displays the area of interest from the first modality image on the second modality image.

Accordingly, on a single user display, an area of interest from a first modality image is displayed within a second modality image.

Preferably, the area of interest from the first modality image corresponds to the same area of interest on the second modality image.

Preferably, the images are correlated.

Preferably, the areas of interest can be regions of interest or volumes of interest.

Preferably, the first modality image and second modality image are two dimensional (2D), three dimensional image (3D), and/or 4 dimensional (4D) images.

Preferably, the first modality image and second modality image originate from a common modality system.

Alternatively, the first modality image and second modality image originate from different modality systems.

As such, the inventive arrangements allow users to view different images of an area of interest on a single screen or viewing port. Combined areas of interest can also be singularly displayed.

These, and other, features and advantages of the inventive arrangements will become more readily apparent from the following detailed description, particularly when taken in conjunction with the drawings and claims herein.

DETAILED DESCRIPTION OF INVENTIVE ARRANGEMENTS

The inventive arrangements will be described with respect to the use of certain modalities as examples of the operation and function hereof. However, it will be readily apparent that the inventive arrangements can also be used with other modalities and combinations thereof, particularly without departing from the spirit and scope hereof. For example, while exemplary embodiments describe the inventive arrangements according to two imaging modalities, any number of modalities can be similarly utilized and fall within the spirit and scope hereof.

Figure 1:
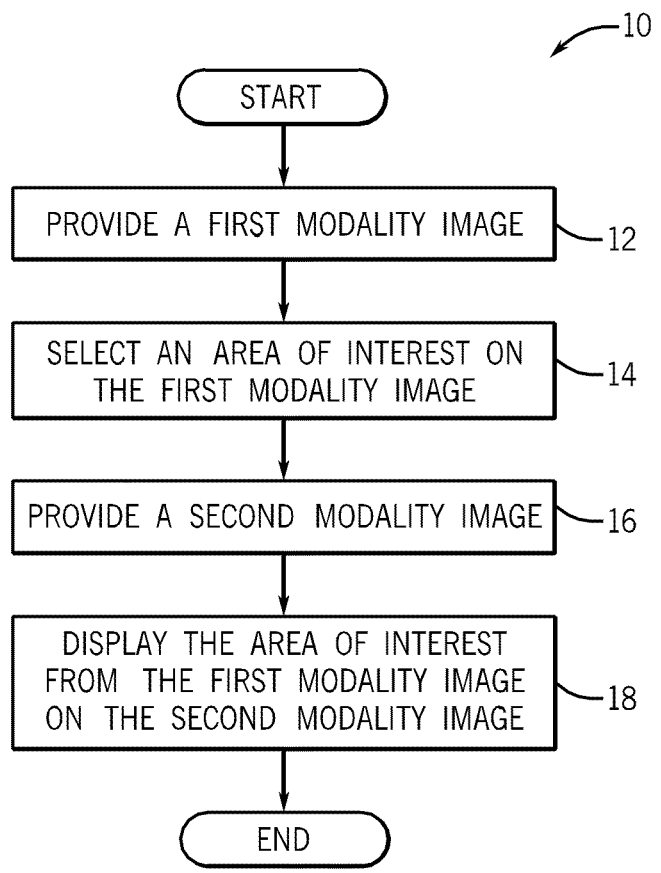
FIG. 1 depicts a method of displaying an area of interest from a first modality image on a second modality image.

Referring now to FIG. 1, a method 10 of displaying an area of interest from a first modality image on a second modality image is illustrated. More specifically, the method 10 comprises providing a first modality image 12, selecting an area of interest on the first modality image 14, providing a second modality image 16, and displaying the area of interest from the first modality image on the second modality image 18, after which the method 10 ends.

Figure 2:
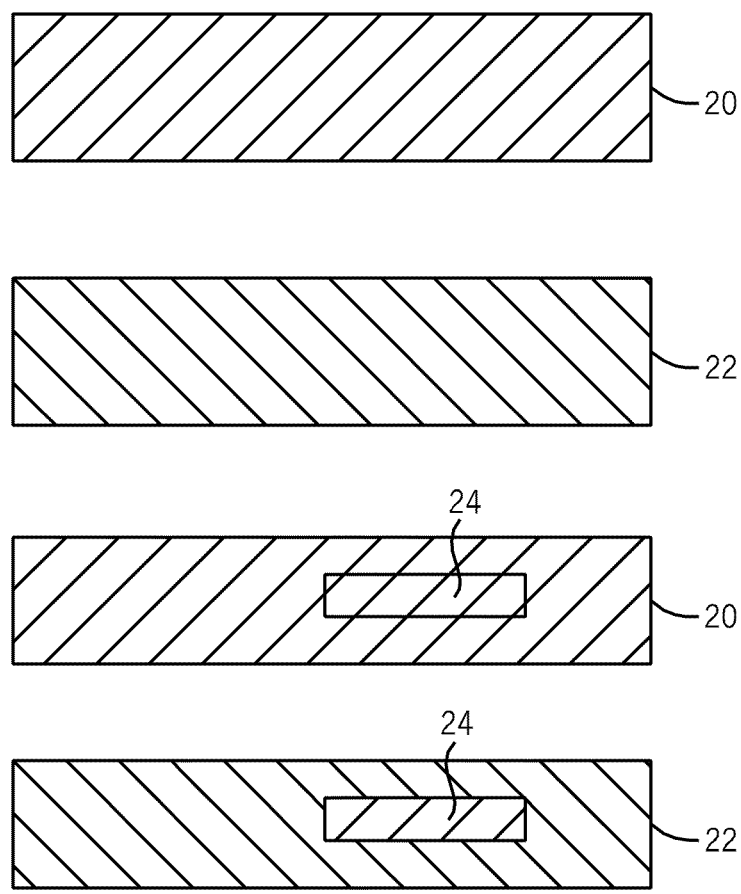
FIG. 2 depicts a single screen display of an area of interest from a first modality image on a second modality image.

Referring now to FIG. 2, a single screen display of an area of interest from a first modality image is displayed on a second modality image. More specifically, a first modality image 20 and second modality image 22 are obtained. The first modality image 20 and second modality image 24 can be obtained separately or in combination. In any event, an area of interest 24 is identified within or on the first modality image 20, which may be a region of interest or volume of interest, which is then projected on the second modality image 22, such that the area of interest 24 projected on the second modality image 22 corresponds to the area of interest 24 identified in the first modality image 20.

Figure 3:
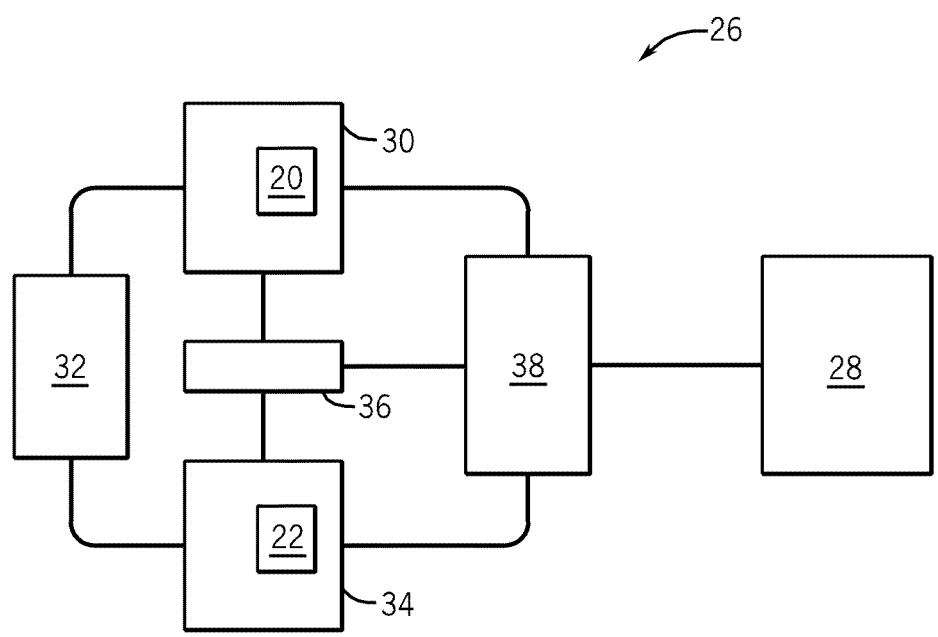
FIG. 3 depicts a system for implementing the inventive arrangements of FIGS. 1-2.

Referring now to FIG. 3, a system 26 comprises a screen 28 for displaying the first modality image 20, the second modality image 22, and/or the area of interest 24. More specifically, the system 26 comprises the screen 28 for displaying images, as well as a first modality imaging system 30 for obtaining the first modality image 20 of a subject 32 and a second modality imaging system 34 for obtaining the second modality image 22 of the subject 32. In this context, the first modality imaging system 30 and second modality imaging system 34 may be separate imaging modality systems, such as x-ray, ultrasound, nuclear medicine imaging (NM), positron emission tomography imaging (PET), computed topography imaging (CT), and/or magnetic resonance imaging (MRI) systems, and/or the like, as well as providing multiple modality images (20, 22) from a common modality (e.g., time-shifted images or images at different energy levels from a common modality origin), in which case the first modality imaging system 30 and second modality imaging system 34 are illustrated conceptually as separate systems (30, 34) for simplicity only, such that multiple modality images (20, 22) are thereby provided about the subject 32 in either instance. In any event, a window delineating the area of interest 24 in the first image 20 is displayed on the second image 22. More specifically, the system 26 includes a means 36 to identify the area of interest 24 in the first modality image 20, as well as a system 38 for simultaneously displaying on the screen 28 an image of the area of interest 24 provided by the first modality imaging system 30 on the second modality image 22, as provided by the second modality imaging system 34.

More detailed examples will now be provided.

Figure 4C:
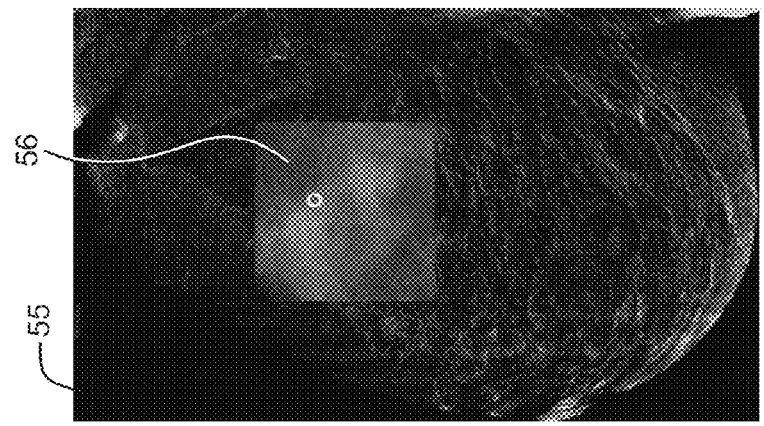
FIGS. 4A-4C depict a multi-modality screen display with representative dual-energy contrast-enhanced digital mammography (CEDM)
Figure 4B:
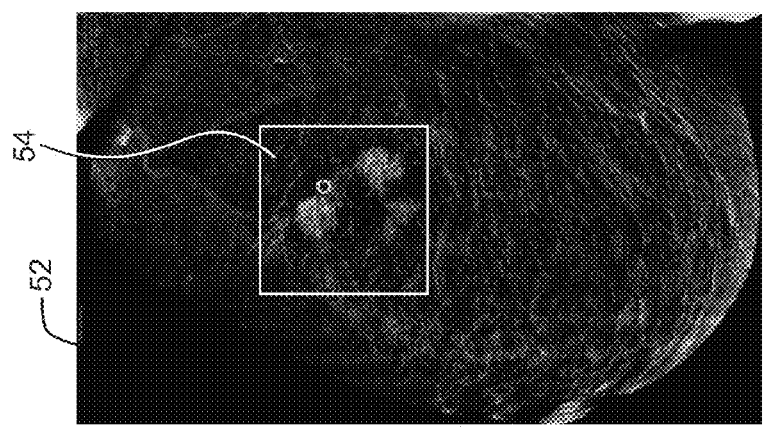
Figure 4A:
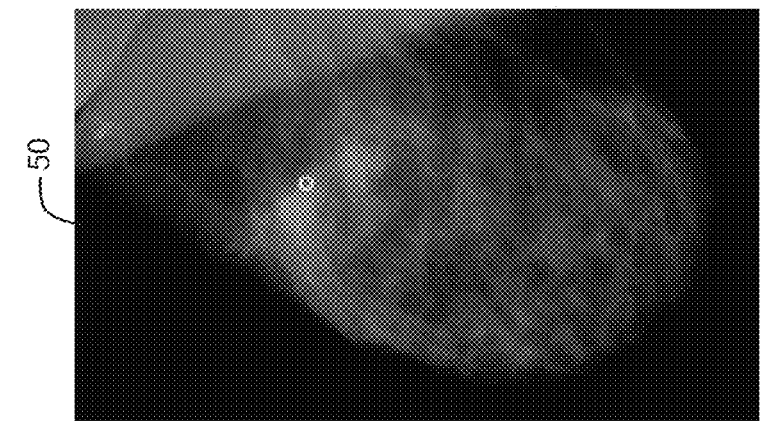

Referring now to FIGS. 4A-4C, differing screen displays depict images that a user could view on a single display utilizing the inventive arrangements with a 2D imaging capability having multiple energy levels—for example, a radiologist performing multiple acquisitions at different energy levels. In dual-energy contrast-enhanced digital mammography (CEDM), for example, the radiologist can perform two different acquisitions of a patient at different energy levels. When reviewing such imagery therefrom, the radiologist may first examine a dual-energy recombined image to search for any possible areas showing enhanced contrast, then seek tissue structure information from a low energy image. Accordingly, in FIG. 4A, for example, a representative low energy image 50 from a low energy scan is depicted. In FIG. 4B, on the other hand, a dual-energy CEDM recombined image 52 is depicted, comprising imagery from both low and high energy scans. As can be seen, the radiologist can place a window in the recombined image 52 to identify a region of interest 54 therewithin. Then, this same region of interest 54 can be identified within the low energy image 50 of FIG. 4A, whereby that portion of the low energy image 50 corresponding to the region of interest 54 in the recombined image 52 can be displayed within that same region of interest 56 identified on the recombined image 52, by which a combined image 55 is displayed in FIG. 4C. Accordingly, the same region of interest 54 from the low energy image 50 is displayed within the recombined image 52, as depicted in FIG. 4C. And if the radiologist iteratively moves the region of interest 54 within the recombined image 52 from FIG. 4B, the corresponding region of interest from the low energy image 50 from FIG. 4A is continually up-dated and displayed in FIG. 4C. In this way, a multi-modality display is provided on a single display.

Figure 5A:
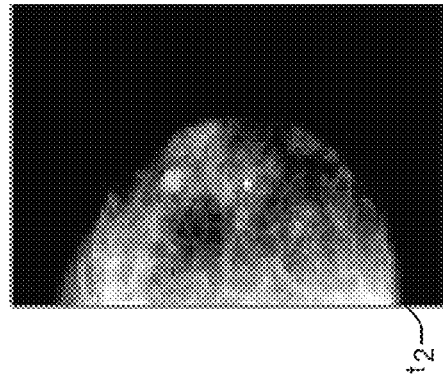
FIG. 5A depicts a mask image.
Figure 5B:
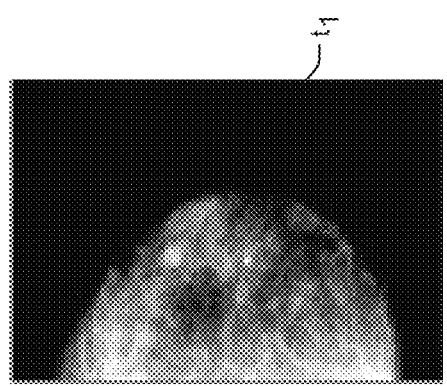
FIG. 5B depicts an opacified image at a first time $t_1$.
Figure 5C:
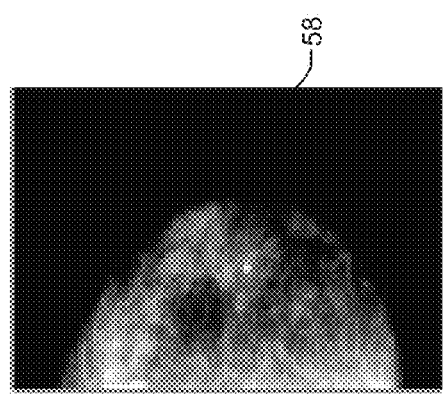
FIG. 5C depicts an opacified image at a first time $t_2$.
Figure 5D:
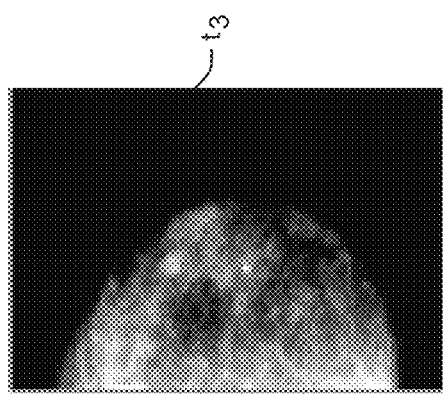
FIG. 5D depicts an opacified image at a first time $t_3$.
Figure 5E:
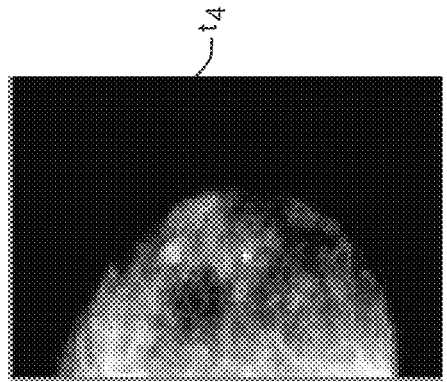
FIG. 5E depicts an opacified image at a first time $t_4$.
Figure 5F:
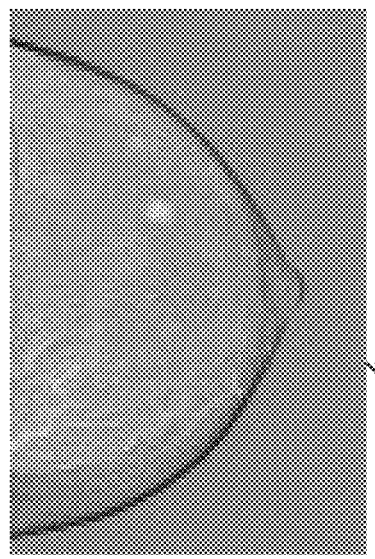
FIG. 5F depicts a subtracted image at the first time $t_1$.
Figure 5G:
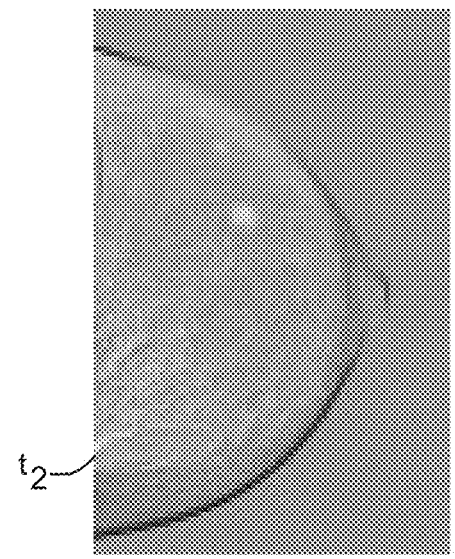
FIG. 5G depicts a subtracted image at the first time $t_2$.
Figure 5H:
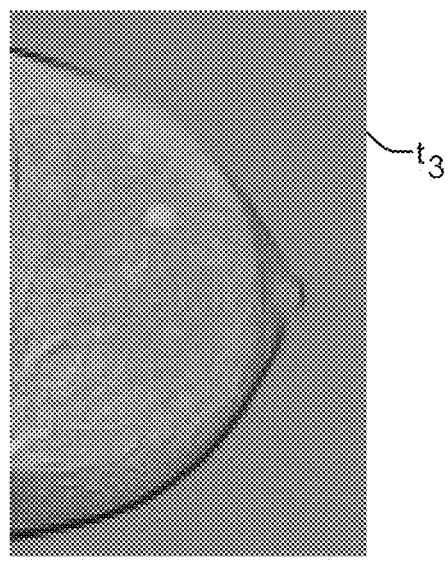
FIG. 5H depicts a subtracted image at the first time $t_3$.
Figure 5I:
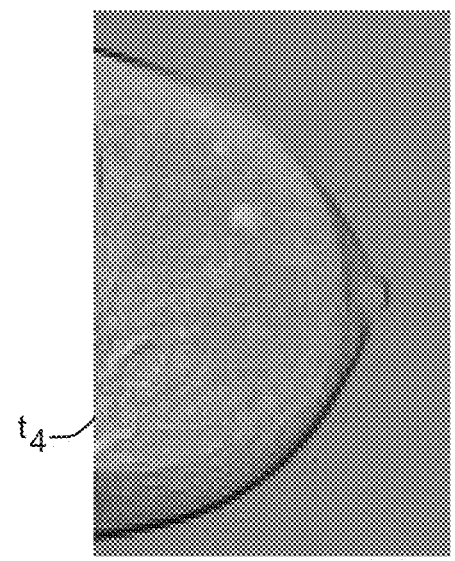
FIG. 5I depicts a subtracted image at the first time $t_4$.
Figure 5K:
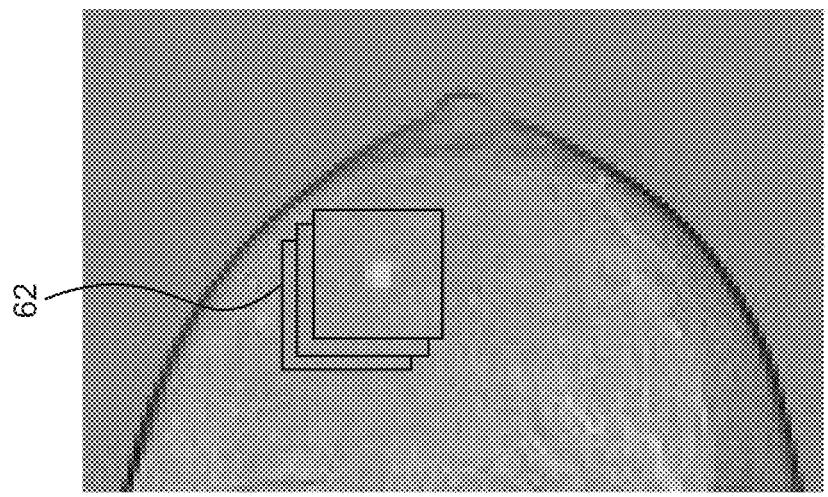
FIG. 5K depicts an cine-loop display of subtracted image sequences cropped to a corresponding area of interest.
Figure 5J:
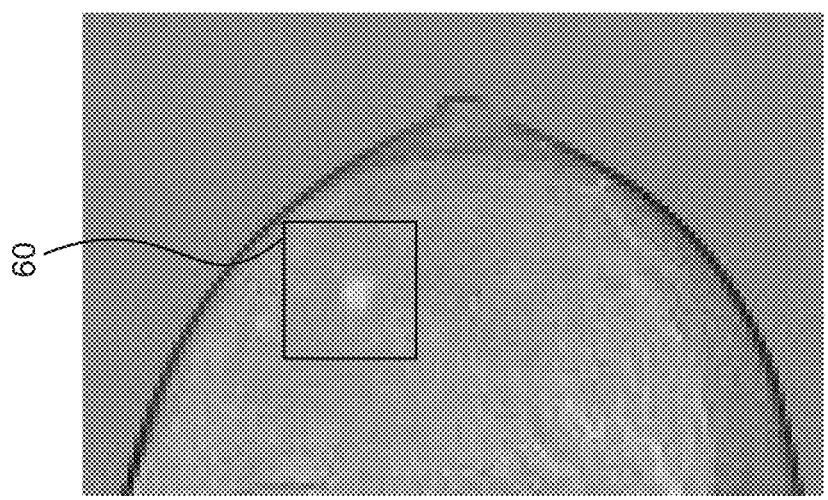
FIG. 5J depicts an area of interest selected on the mask image.

Referring now to FIGS. 5A-5I, they depict various images that can be obtained using temporal CEDM. More specifically, a mask image 58 is depicted in FIG. 5A, representing breast tissue prior to introducing any contrast die materials thereinto. Thereafter, FIGS. 5B-5E respectively depict opacified images at subsequent time intervals $t_1$, $t_2$, $t_3$, and $t_4$, which are image acquisitions taken at sequential time intervals as dye passes into the tissue. FIGS. 5F-5I, in turn, respectively depict the mask image 58 of FIG. 5A, as subtracted from each of the temporal images at $t_1$, $t_2$, $t_3$, and $t_4$. Accordingly, FIG. 5J depicts a screen image in which a user has placed a window to identify a region of interest 60 on the first subtracted image at $t_1$ in FIG. 5F. The user may be interested, for example, in evaluating the evolution of iodine absorption for that specific region of interest 60. Accordingly, corresponding regions of interest 60 are identified in each of the opacified images of FIGS. 5B-5E, for which a combination (e.g., log subtraction) of each opacified region of interest 60 with the mask region of interest may be performed. In FIG. 5K, for example, the subtracted regions of interest 60 are successively displayed inside in a cine-loop 62 within the window starting with the first subtracted image at $t_1$ in FIG. 5F.

Figure 6A:
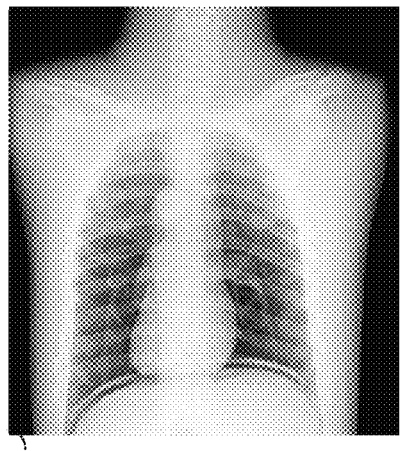
FIG. 6A depicts a low-energy radiological image.
Figure 6B:
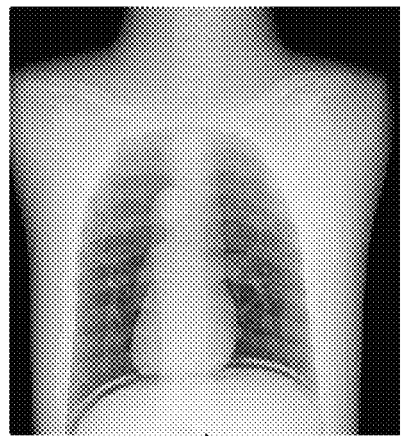
FIG. 6B depicts a high-energy radiological image.
Figure 6C:
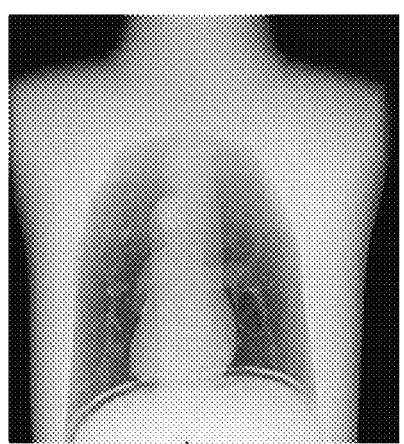
FIG. 6C depicts a combined soft-tissue image.
Figure 6D:
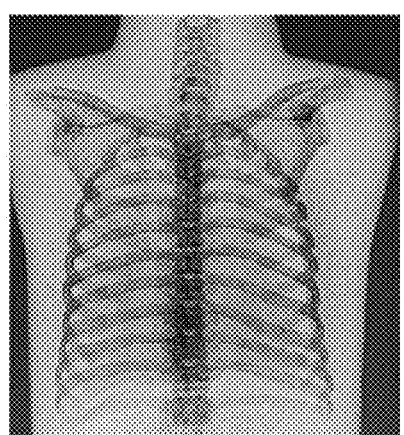
FIG. 6D depicts a combined bone image.
Figure 6F:
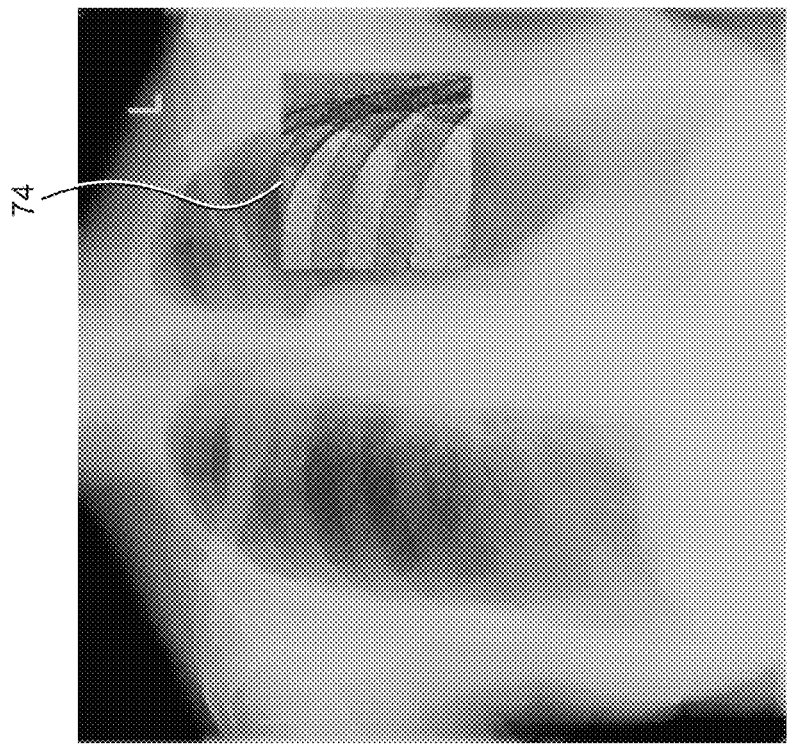
FIG. 6F depicts a bone image inside an area of interest of a low-energy image.
Figure 6E:
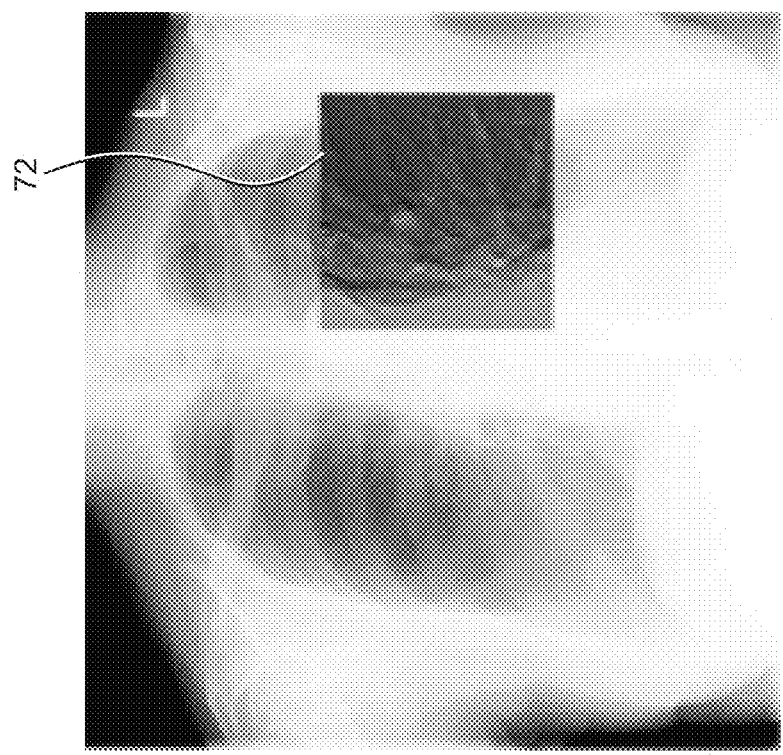
FIG. 6E depicts a soft tissue image inside an area of interest of a low-energy image.

Referring now to FIGS. 6A-6F, they depict representative use of the inventive arrangements with a radiological application. More specifically, in dual-energy radiology applications, for example, both soft-tissue images and bone images can be respectively derived from low energy and high energy images. For example, FIG. 6A depicts a low energy x-ray image 64, while FIG. 6B depicts a high energy x-ray image 66. FIG. 6C depicts a combined soft tissue image 68, while FIG. 6D depicts a combined bone image 70. In FIG. 6E, a user has interactively placed a window indicating a region of interest 72, and in FIG. 6F, the corresponding bone image from FIG. 6D is displayed within the window to cross-modality depict the region of interest 74. In this example, the background image is the soft tissue image 68 from FIG. 6C, while bone information is displayed only inside the window about the region of interest 74. The reverse composition is also possible, particularly as needed and/or desired. Accordingly, a combination of the soft-tissue image 68 from FIG. 6C and the combined bone image 70 from FIG. 6D can be displayed simultaneously on a single screen. If needed and/or desired, transparency constraints can also be applied by techniques known in the art to further enhance the imagery. Likewise, identifying the position of the corresponding region of interest 72 in the second modality image may require a rigid or elastic registration algorithm. An additional manual registration (e.g., a pixel shift) may also be required to further adjust any automatic registrations. Finally, automated systems may also be used to place windows on findings for different modalities.

As described, the first and second imaging modalities (30, 34) from FIG. 3 can be a single modality application, such as a dual-energy acquisition within a single modality, or they can be separate imaging modality systems. They can also be two dimensional (2D), three dimensional image (3D), and/or 4 dimensional (4D) imaging modalities, including any various combinations thereof.

Referring now to using the inventive arrangements with two separate 3D modalities, for example, images may need to be spatially correlated, in which the following steps can be taken: display a slice or slab image obtained from a first modality volume; interactively place a window delineating a region of interest in the first modality image; compute an initial volume of interest corresponding to the selected region of interest; identify the corresponding volume of interest in a second modality volume; and then display into the region of interest selected on the first modality image one or more of the following things:

a) as to slice images of a corresponding volume of interest, sets of slices (or a subset thereof) can be displayed simultaneously on another region of the screen 28 to show information contained within the volume of interest.

b) a slab can be obtained by combining slices of corresponding volumes of interest. The slab can be computed by applying a maximum intensity projection (MIP) operator (or average or any other appropriate transformations) along a z-axis. The slab can also be computed by considering voxel intensity along a ray path going from a source to a detector. A slab or 3D display of a corresponding volume of interest thus depends on one of a maximum value, minimum value, average value, or any mathematical combination of intensity levels for a plurality of pixel or volume elements located along a direction parallel to a ray path extending from a virtual source to a virtual detector.

c) a 3D display of a corresponding volume of interest for several camera positions can be obtained using a MIP operator (or average or any other appropriate transformations). In the particular case of tomosynthesis, for example, a 3D view can be restricted to a limited angular range (e.g., a tumble view) to avoid displaying too many artifacts of reconstruction. If needed or desired, the angular range can be linked to an aperture angle of an acquisition system.

Now then, if images of multiple volumes are not directly spatially correlated, for example, a rigid or elastic registration algorithm can be used to identify corresponding volumes of interest in a second modality volume.

A first modality volume of interest can also be defined manually or automatically with a CAD system. When using a CAD system, for example, a volume of interest's position, width, height, and depth can be automatically defined. When manually defined, on the other hand, the width and height of the volume of interest can be determined from displaying a first modality slice or slab, for example, by moving the corners of a 2D window.

At least several methods for defining depths of volumes of interest are possible, such as the following:

a) depth can be defined on views orthogonal to a slice plane. However, with such views, reconstruction artifacts can degrade informational content due to limited angles of acquisition.

b) z-min and z-max values can be set in indicating the beginning and ending slices of a lesion. For example, a radiologist may go through a volume of interest from a first slice of a lesion and then activate a selection to store it. Subsequently, the radiologist may also indicate a last slice for the lesion and store it after sequencing through spatially correlated image planes.

c) depth can also be set to a default value corresponding to an average size of lesions.

d) depth can also be defined as equal to a thickness of a first modality slab.

e) depth can also be defined as a function of window's width and/or height. In this case, for example, quasi isotropy of lesions of interest can be utilized. In a particular implementation, such as when using a squared window, for example, a corresponding cubic volume of interest can be defined in considering depth equal to width and height. A current slice of interest may then correspond to a central slice of the volume of interest.

Figure 7B:
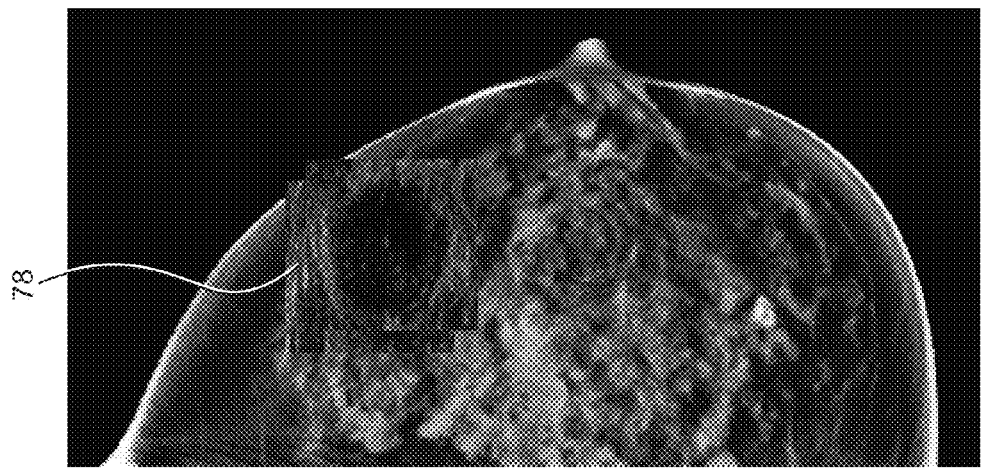
FIG. 7B depicts a volume of interest's centroid on the slice of FIG. 7A, in which slices of the corresponding volume of interest in an ultrasound acquisition are displayed inside the area of interest.
Figure 7A:
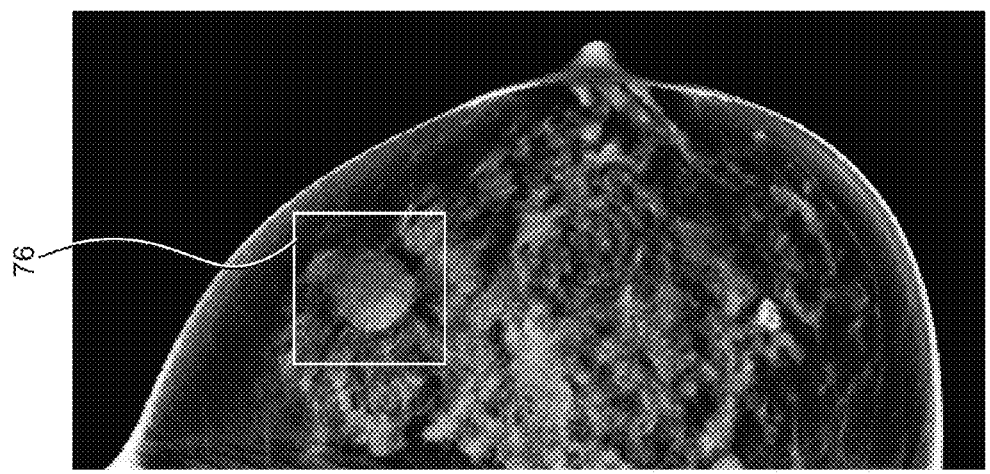
FIG. 7A depicts an x-ray tomosynthesis slice display with a squared area of interest around a lesion.

Referring now to FIGS. 7A-78, they depict representative use of the inventive arrangements with an x-ray tomosynthesis application. More specifically, when reviewing an x-ray reconstructed volume, a user could interactively place a squared window, such as shown in FIG. 7A, to delineate a region of interest 76 on a current slice or slab. A volume of interest can then be inferred from the position of the region of interest. The thickness of the volume of interest can be tuned by the user (e.g., setting a default depth value equal to slab thickness or average lesion thickness). Thereafter, a corresponding volume of interest in an ultrasound volume can be computed. The user can thus examine the slices of the corresponding volume of interest or request a 3D display of the volume of interest inside a 2D window 78, as shown in FIG. 7B.

Now then, in practice, for example, volumes of interest can be displayed with optional segmentation algorithms to highlight lesions or display surface and/or volume renderings of segmented lesions. Volumes of interest can also be optionally enhanced using a high-resolution, on-the-fly reconstruction algorithm, computing a combination of initial and corresponding volumes of interest.

Several volumes of interest can also be defined simultaneously in a volume. Results of any processing applied on a volume of interest and displayed on a 2D window (e.g., a slab with MIP/average, cine-loop, a 3D view of a standard or high-resolution reconstructed, enhanced, and/or segmented volume) can also be exported for editing, printing, and/or including in a presentation using a standard image or video format, all by techniques known in the art. Processed volumes of interest can be individually exported as well, as can exporting in a single image (e.g., in re-projecting volume of interest frames) that indicates relative positions in a volume.

Information used to retrieve a processed volume of interest (e.g., a position of the volume of interest, applied processing techniques, etc.) can also be exported as a saved state for subsequent review on a review workstation or PACS system. Additional information concerning volumes of interest that could be provided by a radiologist and/or a CAD system (e.g., a type of finding (mass or cluster of microcalcifications), a BI-RAD code, lesion size, etc.) could also be exported with other volume of interest information.

As an additional example, when comparing a tomosynthesis exam with a 2D acquisition (the 2D acquisition could be from a prior acquisition of a particular projection acquired during a tomosynthesis sweep), a user can interactively place a window delineating a region of interest in a current slice or slab of a tomosynthesis volume. A corresponding region of interest in a 2D acquisition can be computed automatically by re-projecting the region of interest boundaries according to a 0° source position (i.e., perpendicular to a detector). Such a re-projection operation can account for magnification due to system geometries. Additional manual and/or automatic registration may also be performed, and the content of corresponding regions of interest can be displayed inside a window on a current slice or slab. In this example, a background image displayed on a screen may be a tomosynthesis slice or slab. 2D prior information can be displayed inside the window, as can converse applications. And finally, CAD systems can be used to identify positions of lesion along z-axes.

Those skilled in the art will readily recognize that numerous adaptations and modifications can be made to the inventive arrangements, comprising displaying multi-modality information on a common screen or display, which will result in additional arrangements which fall within the scope and spirit hereof as defined in the following claims. Accordingly, the inventive arrangements are only limited by the following claims and their equivalents.

What is claimed is:

1. A method of displaying image data of an imaged subject, comprising:
   displaying a first modality image on a screen of an image review system;
   receiving a user selection of an area of interest in the first modality image, wherein the area of interest is a portion of the first modality image that is less than the entirety of the first modality image and that depicts an anatomic region;
   displaying a second modality image on a screen of an image review system, wherein the first modality image and the second modality image each depict the anatomic region;
   identifying a corresponding area of interest in the second modality image that depicts the anatomic region;
   displaying the area of interest from the first modality image over the corresponding area of interest in the second modality image such that the corresponding area of interest in the second modality image depicts the anatomic region as it appears in the first modality image; and
   updating the display of the area of interest over the corresponding area of interest in response to receiving an update user selection of the area of interest in the first modality image;
   wherein the first modality image and the second modality image are acquired from separate imaging systems of different types.

2. The method of claim 1, wherein the area of interest from the first modality image is simultaneously displayed within the second modality image.

3. The method of claim 1, wherein the area of interest in the first modality image and the corresponding area of interest in the second modality image are correlated, such that displaying the area of interest from the first modality image within the second modality image displays commonality therebetween.

4. The method of claim 1, wherein the area of interest is a region of interest or volume of interest.

5. The method of claim 1, wherein the first modality image is selected from a group consisting of a two dimensional (2D), three dimensional image (3D), and 4 dimensional (4D) image.

6. The method of claim 1, wherein the second modality image is selected from a group consisting of a two dimensional (2D), three dimensional image (3D), and 4 dimensional (4D) image.

7. A system for displaying image data of an imaged subject, comprising:
   a screen;
   a selector configured to allow user selection of an area of interest in a first modality image when the first modality image is displayed on the screen, wherein the area of interest is a portion of the first modality image that is less than the entirety of the first modality image and that depicts an anatomic region;
   an image display subsystem configured to identify a corresponding area of interest that depicts the anatomic region in a second modality image and to display the selected area of interest from the first modality image over the corresponding area of interest in the second modality image when the second modality image is displayed on the screen, such that the corresponding area of interest in the second modality image depicts the anatomic region as it appears in the first modality image, wherein the image display subsystem is configured to update the display of the area of interest over the corresponding area of interest in response to receiving an update user selection of the area of interest in the first modality image;
   wherein the first modality image and the second modality image are acquired from separate imaging systems of different types in communication with the system.

8. The system of claim 7, wherein the screen displays the area of interest from the first modality image simultaneously within the second modality image.

9. The system of claim 7, wherein the area of interest in the first modality image and the corresponding area of interest in the second modality image are correlated, such that displaying the area of interest from the first modality image within the second modality image displays commonality therebetween.

10. The system of claim 7, wherein the area of interest is a region of interest or volume of interest.

11. The system of claim 7, wherein the first imaging modality is selected from a group consisting of a two dimensional (2D), three dimensional image (3D), and 4 dimensional (4D) imaging modality.

12. The system of claim 7, wherein the second imaging modality is selected from a group consisting of a two dimensional (2D), three dimensional image (3D), and 4 dimensional (4D) imaging modality.

13. The method of claim 1, wherein identifying the corresponding area of interest in the second modality image comprises registering the first modality image and the second modality image at least at the anatomic region.

14. The method of claim 1, comprising scaling one or both of the area of interest or the corresponding area of interest such that the anatomic region is depicted as being substantially the same size in both the area of interest or the corresponding area of interest.

* * * * *